(12) United States Patent
Liberti et al.

(10) Patent No.: US 11,413,378 B2
(45) Date of Patent: Aug. 16, 2022

(54) RIGID CHAMBER FOR CELL SEPARATION FROM A FLEXIBLE DISPOSABLE BAG

(71) Applicants: BIOMAGNETIC SOLUTIONS LLC, State College, PA (US); Joseph Francis Liberti, Harrison, NY (US)

(72) Inventors: Paul A Liberti, Naples, FL (US); Dustin W Ritter, State College, PA (US)

(73) Assignee: BioMagnetic Solutions LLC, State College, PA (US)

( * ) Notice: Subject to any disclaimer, the term of this patent is extended or adjusted under 35 U.S.C. 154(b) by 0 days.

(21) Appl. No.: 17/052,717

(22) PCT Filed: May 8, 2018

(86) PCT No.: PCT/US2018/031586
§ 371 (c)(1),
(2) Date: Nov. 3, 2020

(87) PCT Pub. No.: WO2019/216887
PCT Pub. Date: Nov. 14, 2019

(65) Prior Publication Data
US 2021/0220533 A1 Jul. 22, 2021

(51) Int. Cl.
*A61M 1/02* (2006.01)
*A61M 1/36* (2006.01)
(Continued)

(52) U.S. Cl.
CPC .............. *A61M 1/0209* (2013.01); *A61J 1/16* (2013.01); *A61M 1/3618* (2014.02); *G01N 33/585* (2013.01)

(58) Field of Classification Search
CPC .............. A61M 1/0209; A61M 1/3618; A61M 2202/0437; A61M 2202/0413;
(Continued)

(56) References Cited

U.S. PATENT DOCUMENTS 3,838,794 A 10/1974 Cogley
3,970,517 A 7/1976 Van Nederveen
(Continued)

FOREIGN PATENT DOCUMENTS

EP 438520 8/1994
EP 1058564 12/2000
(Continued)

OTHER PUBLICATIONS

European Examination Report in EP application 1 6 793 340. 7 dated Nov. 19, 2019.
(Continued)

*Primary Examiner* — Adam Marcetich
(74) *Attorney, Agent, or Firm* — Howson & Howson LLP

(57) ABSTRACT

Method consists of placing a flexible container within a rigid frame and expanding the container by pneumatic or hydraulic pressure such that the walls of the container conform to the inside walls of the rigid frame thus forming a well-defined chamber. The system has the capability of reducing the volume of the chamber by adjusting the distance between the walls of the rigid container. The methods and systems so described are applicable to closed sterile systems that employ immunomagnetic isolation or purging of components from blood products. By providing a fixed volume and at least one surface upon which targeted entities can be magnetically deposited, target cells in the case of positive isolations can be magnetically held, flushed with wash buffers over them to remove entrapped cells and finally the recovery of product of very high purifies and at high yields.

19 Claims, 5 Drawing Sheets

(51) Int. Cl.
*A61J 1/16* (2006.01)
*G01N 33/58* (2006.01)

(58) Field of Classification Search
CPC .............. A61M 2202/0429; A61J 1/16; G01N 33/54326; G01N 33/491; G01N 33/4915; G01N 1/34; B03C 2201/26; B03C 1/002; B03C 1/08; B03C 1/04; C12M 47/04
See application file for complete search history.

(56) References Cited

U.S. PATENT DOCUMENTS

| | | | |
|---|---|---|---|
| 4,018,886 A | 4/1977 | Giaever | |
| 4,230,685 A | 10/1980 | Senyei | |
| 4,267,234 A | 5/1981 | Rembaum | |
| 4,375,407 A | 3/1983 | Kronick | |
| 4,452,773 A | 6/1984 | Molday | |
| 4,554,088 A | 11/1985 | Whitehead | |
| 4,654,267 A | 3/1987 | Ugelstad | |
| 4,659,678 A | 4/1987 | Forrest | |
| 4,710,472 A | 12/1987 | Saur | |
| 4,795,698 A | 1/1989 | Owen | |
| 4,866,282 A * | 9/1989 | Miripol | A61M 1/3681 250/455.11 |
| 4,904,391 A | 2/1990 | Freeman | |
| 4,910,148 A | 3/1990 | Sorensen | |
| 4,935,147 A | 6/1990 | Ullman | |
| 4,988,618 A | 1/1991 | Li | |
| 5,163,909 A | 11/1992 | Stewart | |
| 5,186,827 A | 2/1993 | Liberti | |
| 5,297,234 A * | 3/1994 | Harms | A23L 3/365 392/379 |
| 5,399,166 A | 3/1995 | Laing | |
| 5,466,574 A | 11/1995 | Liberti | |
| 5,510,621 A * | 4/1996 | Goldman | G01N 21/51 250/339.12 |
| 5,514,340 A | 5/1996 | Lansdorp | |
| 5,536,475 A | 7/1996 | Moubayed | |
| 5,541,072 A | 7/1996 | Wang | |
| 5,567,326 A | 10/1996 | Ekenberg | |
| 5,597,531 A | 1/1997 | Liberti | |
| 5,660,990 A | 8/1997 | Rao | |
| 5,693,539 A | 12/1997 | Miltenyi | |
| 5,698,271 A | 12/1997 | Liberti | |
| 5,799,830 A | 9/1998 | Carroll | |
| 5,968,820 A | 10/1999 | Zborowski | |
| 6,036,857 A | 3/2000 | Chen | |
| 6,120,856 A | 9/2000 | Liberti | |
| 6,126,835 A * | 10/2000 | Barbera-Guillem | B03C 1/0332 210/695 |
| 6,129,848 A | 10/2000 | Chen | |
| 6,132,607 A | 10/2000 | Chen | |
| 6,190,913 B1 * | 2/2001 | Singh | B01F 11/0017 435/383 |
| 6,245,570 B1 * | 6/2001 | Grimm | A61J 1/10 250/453.11 |
| 6,432,630 B1 | 8/2002 | Blankenstein | |
| 6,551,843 B1 | 4/2003 | Rao | |
| 6,576,458 B1 * | 6/2003 | Sarem | C12M 23/34 435/286.5 |
| 6,764,859 B1 | 7/2004 | Kreuwel | |
| 2002/0058030 A1 * | 5/2002 | Monroy | A61M 1/3618 424/140.1 |
| 2003/0060747 A1 * | 3/2003 | Fries | A61M 1/3681 210/748.11 |
| 2003/0127396 A1 | 7/2003 | Siddiqi | |
| 2004/0124157 A1 * | 7/2004 | Briggs | A61M 1/0227 210/787 |
| 2004/0186412 A1 * | 9/2004 | Mallett | A61M 1/3482 604/6.08 |
| 2005/0121604 A1 | 6/2005 | Mueth | |
| 2005/0186669 A1 * | 8/2005 | Ho | C12M 23/14 435/287.1 |
| 2007/0042490 A1 * | 2/2007 | Welter | C12N 5/0655 435/325 |
| 2007/0125942 A1 | 6/2007 | Kido | |
| 2009/0053799 A1 | 2/2009 | Chang-Yen | |
| 2009/0188211 A1 * | 7/2009 | Galliher | B01F 15/0085 53/434 |
| 2009/0220932 A1 | 9/2009 | Ingber | |
| 2010/0081122 A1 * | 4/2010 | Shibuya | C12M 41/46 435/3 |
| 2010/0112700 A1 * | 5/2010 | Shaaltiel | C12M 41/34 435/410 |
| 2011/0020459 A1 | 1/2011 | Achrol | |
| 2011/0124128 A1 | 5/2011 | Oosterbroek | |
| 2011/0165666 A1 * | 7/2011 | Dahle | C12M 23/26 435/292.1 |
| 2014/0370592 A1 | 12/2014 | Miltenyi | |
| 2015/0064703 A1 | 3/2015 | Super | |
| 2015/0153259 A1 | 6/2015 | Liberti | |
| 2016/0015599 A1 | 1/2016 | Gentile | |
| 2017/0029776 A1 * | 2/2017 | Cork | A61M 1/3683 |
| 2017/0315121 A1 | 11/2017 | Wegener et al. | |
| 2017/0335272 A1 | 11/2017 | Tsai | |
| 2018/0172685 A1 * | 6/2018 | Wegener | A61M 1/0281 |
| 2019/0010435 A1 * | 1/2019 | Norderhaugh | A61M 1/3618 |
| 2019/0169594 A1 * | 6/2019 | Zhang | B03C 1/01 |

FOREIGN PATENT DOCUMENTS

| | | | |
|---|---|---|---|
| EP | 3238760 A1 | 11/2017 | |
| WO | 1991011716 | 8/1991 | |
| WO | WO-2017116910 A1 * | 7/2017 | ............ C12M 23/26 |

OTHER PUBLICATIONS

International Preliminary Report on Patentability issued in PCT/US16/31528 dated Nov. 14, 2017.
International Search Report & Written Opinion issued in PCT/US18/31586 dated Jul. 31, 2018.
International Search Report issued in PCT/US16/31528 dated Aug. 18, 2016.
Response to 1st Office Action dated Jul. 19, 2019 in corresponding CN application # 201680026632.
Response to 2nd Office Action dated Jan. 22, 2020 in corresponding CN appliation # 201680026632.
Response to 3rd Office Action dated Jun. 28, 2020 in corresponding CN appliation # 201680026632.
1st Office Action dated Jul. 19, 2019 in corresponding CN application # 201680026632.
2nd Office Action dated Jan. 22, 2020 in corresponding CN appliation # 201680026632.
3rd Office Action dated Jun. 28, 2020 in corresponding CN appliation # 201680026632.
International Search Report & Written Opinion Issued in PCT/US20/59062 dated Mar. 11, 2021.
Extended European Search Report issued in EP Patent Application No. 18918317.1 dated Apr. 7, 2021.

* cited by examiner

RIGID CHAMBER FOR CELL SEPARATION FROM A FLEXIBLE DISPOSABLE BAG

RELATED APPLICATIONS

This application is a national stage application under 35 U.S.C. 371 for International Application No. PCT/US18/31586, filed May 8, 2018, the entire contents of which application are incorporated herein by reference.

FIELD OF THE INVENTION

This invention relates to converting a flexible container into a substantially rigid container. In particular, it relates to converting flexible bags in a closed-system disposable bag set into substantially rigid containers with at least one surface for the collection of magnetic entities in a reproducible fashion for performing immunomagnetic cell separations from leukapheresis products, peripheral blood, and bone marrow, and more particularly to novel methods in the use of such bag sets for the multiple steps required to perform such separations under sterile conditions.

BACKGROUND OF THE INVENTION

Immunomagnetic cell separations can be performed using internal or external magnetic gradient devices. Internal magnetic gradients are created by placing ferromagnetic objects (typically iron or nickel spheres, rods, or wool) within an external magnetic field, the physics of which are well known. Using Maxwell's equations, it can be shown that the smaller the diameter of the sphere, rod, or wool, the greater the magnetic gradient that is induced and the smaller the reach of that induced magnetic gradient. Internally generated magnetic gradients exceeding 100 kGs/cm are readily created. Accordingly, when magnetically labeled cells pass through a column packed with small steel spheres (or appropriately sized rods or wool) while that column is held within an external magnetic field, such cells will be magnetically attracted to those objects. Internal gradient arrangements are typically used when cells are labeled with weakly magnetic colloids such as those produced by Molday (U.S. Pat. No. 4,452,773) and commercialized by Miltenyi Biotec GmbH.

On the other hand, when target cells are immunomagnetically labeled with highly magnetic colloidal nanoparticles, such as those described by Liberti, et al. (U.S. Pat. Nos. 6,120,856; 5,698,271; 5,512,332), they can be separated in magnetic gradients in the range of 6-10 kGs/cm. Such gradients are readily achievable by pole piece design and/or the positioning of magnets relative to one another, thus creating what are referred to as external or open-field magnetic gradient devices into or against which appropriate separation chambers can be placed.

Quadrupole open-field magnetic gradient devices such as those disclosed by Liberti, et al. (U.S. Pat. Nos. 5,186,827; 5,466,574) for immunomagnetic separation are well known in the art and conveniently allow a vessel to be placed within a magnetic field with a radial gradient which causes magnetically labeled entities to be pulled radially to the inner walls of a vessel. Bucking magnet arrangements, and many others, have been used to create surfaces that pull magnetic entities toward them; thus magnetically labeled entities can be isolated on one side of a container (U.S. Pat. No. 5,536,475). In a co-pending application PCT/US2016/031528, rare-earth block magnets (200×5×20 mm, magnetized through the 20 mm dimension) are arranged parallel to each other, spaced 3 mm apart, with alternating polarities and with the 5×200 mm sides affixed to an iron backing plate (32×22 cm). This array creates powerful magnetic gradients such that when a suitable chamber is brought into contact with the planar surface created by the alternating poles, magnetic entities collect on the inside wall of the container that is adjacent to that magnetic gradient surface. An array of this type benefits from the use of a companion chamber that is rectilinear in shape because in such a chamber, target cells within any given plane above the array experience approximately the same magnetic gradient force, promoting uniform collection across the chamber collection surface.

For macromolecular targets labeled with magnetic nanoparticles such as the Liberti ferrofluids (115-160 nm), it has been demonstrated that they can advantageously be collected in quasi-monolayers using cylindrical tubes in quadrupole magnetic devices (U.S. Pat. No. 5,660,990) which create extremely uniform radial gradients. In many cases, undesired components that are collected along with targets can readily be swept away merely by streaming appropriate buffers over targeted elements held in place by magnetic forces. That ability obviates having to move the separation chamber out of the magnetic field, re-suspend all the magnetically collected material, and move the chamber back into the magnetic gradient to effect subsequent magnetic separations. That is typically how such purifications are done with larger magnetic particles using open-field magnetic gradient arrangements; with each subsequent magnetic separation, undesired components remain suspended in the supernatant and are discarded.

Clearly, the task of purifying cellular targets is more difficult given the fact that cells have many more complex properties than the simple macromolecules involved in various immunoassays disclosed in U.S. Pat. No. 5,660,990. From extensive studies with magnetically collected cells, it has been discovered that entrapped undesired or "bystander" cells collected in small numbers of layers can indeed be removed without re-suspending them. However, streaming buffer over such collected cells with the additional movement of menisci (or bubbles) over such collected cells provides an additional "scrubbing" effect which greatly improves the removal of bystander cells.

For the immunomagnetic separation of cells from a patient where the cells will be sterilely processed and eventually returned to the patient or used in some other manner requiring sterility, it is essential to work within a closed system. To perform an immunomagnetic selection with subsequent harvest of the desired cells, numerous procedural steps are required, such as 1) labeling of cells (which can be a multi-step process); 2) magnetic separation; 3) removal of non-targeted components; 4) subsequent removal of bystander cells that might have been unintentionally captured during the separation process; and 5) recovery of the positive fraction containing the desired cells. An efficient means for creating a closed system capable of performing the various required steps has been to use plastic bag-like chambers interconnected by plastic tubing. Thus, by appropriate valves and pumps, the various steps can be performed—a concept that is illustrated by Johnson (Eur. Pat. No. 1,058,564).

We have discovered that certain chamber conditions are desirable in order to achieve a magnetic separation wherein entrapped non-target cells can be removed with a minimal number of re-suspension/re-separation steps. There are also some significant issues to resolve if entrapped cells are to be dislodged effectively. One such requirement is that the surface of the separation chamber upon which cells are collected must stay in close proximity with the magnetic surface throughout the entirety of the process. This is essential because the effective magnetic "reach" of such magnetic arrays is relatively short (typically 7-10 mm), beyond which the magnetic gradient falls off sharply. Hence, should the collection surface be separated from the magnetic surface by even a few millimeters, target cells will be dislodged, resulting in considerable losses of targets during the washing process.

For many immunomagnetic cell separations that employ relatively large magnetic particles (>800 nm), a flexible bag containing a cell mixture to be separated can be simply placed against or within a magnetic gradient device to perform a separation, and because target cells are held so tightly, flexible bags can be successfully employed as separation chambers. After pumping or flowing non-target cells from the bag, the magnetic field can be removed and cells can be re-suspended in buffer; by re-applying the magnetic field, cells can be separated again, and this process of re-suspension/re-separation can be repeated as necessary until all bystander cells are eliminated from the bag.

On the other hand, for cells and other targets labeled with magnetic nanoparticles such as the Liberti ferrofluids (115-160 nm), targets will have substantially less magnetic mass per target than those labeled with larger magnetic particles. Consequently, ferrofluid-targeted cells will be more easily dislodged from the surface of a magnetic gradient device than those labeled with larger magnetic particles. Hence, some special considerations must be taken into account as regards the nature of the collection chamber and the magnetics employed. Despite this potential disadvantage, the discovery that target cells can be collected in layers and entrapped bystander cells removed without resuspension makes the construction of a collection chamber from a flexible blood bag extremely desirable as this obviates having to move the chamber out of the magnetic field, re-suspend the cells, and move the chamber back into the magnetic field to effect subsequent magnetic separations. Since such a system also avoids using harsh means to remove impurities, product viability would be expected to be significantly improved, which is indeed the case.

While being able to remove entrapped bystander cells without re-suspension would permit constant engagement of the magnetic gradient device throughout the entirety of the process, it may be advantageous in some cases to disengage the magnetic gradient device from the collection chamber. For example, if a mixture of cells were first introduced into the collection chamber, followed by the introduction of magnetic nanoparticles to label target cells, it would be advantageous for the magnetic gradient device to be sufficiently far away from the collection chamber to allow for the labeling process to occur. Also, if re-suspension with subsequent re-separation was desired, cyclic disengagement and re-engagement of the magnetic gradient device would be required. Finally, disengaging the magnetic gradient device to permit re-suspension of isolated target cells prior to recovery could be advantageous.

The issues in constructing an appropriately sized chamber to collect cells in layers and subsequently process them are nontrivial. In a typical leukapheresis product, there will be $5 \times 10^9$ total nucleated cells (TNC). In the case of isolating T cells or subsets thereof, for example, approximately 50% will be CD3+ cells, a fraction of which will be CD4+ and CD8+(in a ratio of about 2:1, respectively). To monolayer all the CD3+ cells requires about 1600 cm$^2$, which makes the construction of a chamber with an appropriate collection surface area somewhat impractical. However, from studies with ferrofluid-labeled HPB cells (CD3+ cell line) containing significant quantities of erythrocytes (up to 20% hematocrit), it was determined that entrained erythrocytes can be very effectively removed from about five layers of magnetically collected target cells by passing buffer over them. The process is made more efficient by "scrubbing" with a meniscus (formed by an air bubble in the washing buffer) while the collected cells are magnetically held against the side of the chamber. Based on that finding, a collection surface of about 320 cm$^2$ could be used for the above example of a CD3+ cell isolation from a leukapheresis product. In the case of isolating CD34+ stem cells, one might expect to process as many as $5 \times 10^{10}$ TNC, and with a 2% stem cell population, the foregoing surface would collect those cells in about two layers.

Another constraint on a flexible bag collection chamber is that the shape of the container, particularly the collection surface (or surfaces, if magnetic gradients are applied to both sides of the chamber) must be maintained so that the bag can be emptied after the first separation and the washes. Any flexing of the bag during those operations could dislodge target cells by moving them away from the regions of the strongest magnetic gradient.

Ideally, the separation chamber should have a variable capacity to accommodate starting materials containing different numbers of TNC and/or different percentages of target cells. For example, for an isolation of T cells or subsets thereof (e.g., CD4+ T cells), such levels can be quite variable among starting materials (roughly, 30-85% for T cells and 25-65% for CD4+ T cells). In magnetic cell separations, the concentrations of total cells and target cells are important parameters. Hence, there are both optimal concentrations of total cells and target cells that need to be taken into account.

There are two ways to vary the volume of a rectilinear chamber: changing its surface area or changing its depth. For a disposable rectilinear-shaped bag, the volume can be varied by selecting a bag with a fixed depth, but with larger and smaller surface area; these bags would be used in conjunction with a planar magnetic array capable of accommodating the largest bag that is expected to be used. On the other hand, a chamber where the depth can be varied offers several advantages. Not only can the volume be altered to accommodate different TNC counts or target cell densities, but altering the volume by adjusting the depth can be advantageous in processing. For example, if the optimal concentration of TNC for magnetic separation is $3 \times 10^7$ TNC/mL and $9.6 \times 10^9$ TNC are to be processed, a rectangular bag with a depth of 10 mm would need to contain 320 mL. Accordingly, the surface area of one side of the bag would be 320 cm$^2$. On the other hand, if only $6.7 \times 10^9$ TNC are to be processed, the same bag could be used if the depth could be constrained to 7 mm, thereby enabling the same bag set to be used for separations of different numbers of TNC.

Additionally, once target cells are separated, it would be advantageous to decrease the depth of the chamber by bringing the walls of the chamber closer for the following reasons: 1) less buffer would be required to wash the magnetically collected cells; 2) meniscus scrubbing effects are expected to be more effective because of the small contact angle created by bringing the chamber walls nearer to each other; and 3) solution changes will have less boundary mixing if the walls of the bag are closer to each other and, in fact, an air gap can be introduced after a solution has been passed and before the next solution enters the chamber. Placing air gaps between samples or solutions in small diameter tubes is well known in the art for pumping solutions while keeping them separated.

SUMMARY OF THE INVENTION

The present invention provides a method and apparatus for converting a flexible container into a substantially rigid container.

According to one aspect, the present invention provides a method for converting a flexible container into a substantially rigid container. The method may include placing the flexible container into a rigid frame and expanding the container by applying positive pressure to engage the container with the frame. The flexible container may be a disposable bag for aseptically processing cells. The container may be expanded pneumatically or hydraulically. The container may have valved ports on each end to control fluid flow through the container. The walls of the frame may be planar or have surface projections to direct fluid flow through the container, and they may be parallel to one another. The spacing between the walls of the frame may be adjustable. The method may be employed to separate target cells from a mixed cell population by forming a substantially rigid container, introducing the mixed cell population and a magnetic labeling agent, separating magnetically labeled target cells, and recovering the magnetically labeled target cells. The walls of the frame may comprise a magnet component to generate a magnetic field gradient, and this magnetic component may be reversibly disengageable from the walls of the frame to reversibly attenuate the magnetic field gradient. A wash fluid may be passed through the container before recovering the magnetically labeled target cells. The mixed cell population and the magnetic labeling agent may be simultaneously or sequentially introduced into the container.

According to another aspect, the present invention provides a system for converting a flexible container into a substantially rigid container. The system may include a rigid frame and a flexible container which is expansible under the influence of positive pressure. The system may include a pressure source to apply positive pressure. The walls of the frame may be movable to adjust their spacing. The walls of the frame may comprise a magnet component to generate a magnetic field gradient, and this magnetic component may be reversibly disengageable from the walls of the frame to reversibly attenuate the magnetic field gradient.

DETAILED DESCRIPTION OF THE INVENTION

To produce a rigid, sterile chamber to meet the foregoing needs, we disclose herein methods and devices whereby a flexible disposable bag can be converted into a rigid container having a predetermined, reproducible shape and collection surface(s). Further, these methods allow the flexible bag to maintain that predetermined shape throughout a series of manipulations that include filling and emptying of the bag, tilting the bag (useful for a variety of processing steps, particularly the introduction of bubbles with subsequent agitation for meniscus scrubbing), as well as during recovery of the product. We also disclose means for efficiently moving different solutions through the system and particularly within the separation chamber that promote plug flow and minimize mixing at boundaries between such solutions. This is accomplished by employing differential densities of sequential solutions in conjunction with tilting of the chamber to leverage gravitational effects or by decreasing the depth of the chamber and using air gaps to keep solutions separated from one another. These are key considerations for achieving the removal of non-target components and thus purification of the desired product.

Figure 1:
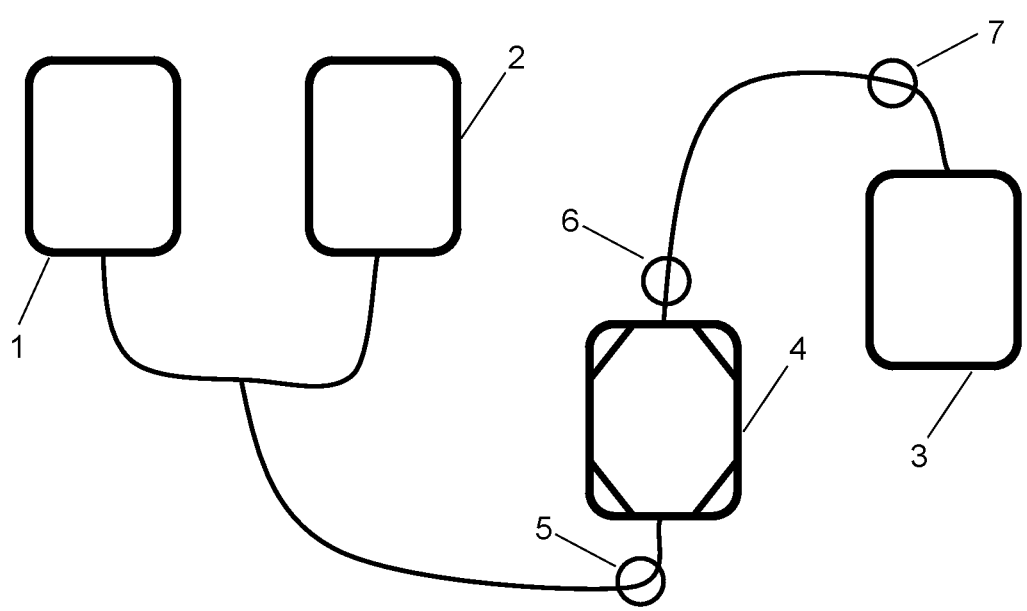
FIG. 1 shows an example of a disposable set of bags with inter-connecting tubing and valves that might be used to perform an immunomagnetic cell separation of some subset of cells derived from leukapheresis product, peripheral blood, bone marrow, or the like. The set consists of a source bag 1 containing the starting material (e.g., blood, leukapheresis product, washed cells, or the like), a buffer reservoir bag 2 that could be used for pushing solutions through the system, for washing away non-target cells, or re-suspension of product, a waste bag 3, and a disposable, rectilinear bag 4 wherein the magnetic separation takes place. Valves 5 and 6 are positioned at the inlet and outlet of the separation bag 4, respectively. A valve 7, which is positioned near the waste bag 3, is employed during the pneumatic pressurization of said waste bag and the subsequent pressurization of the separation bag 4.

FIG. 1 shows a disposable bag set that might be used for positive or negative immunomagnetic cell separations. The set comprises a source bag 1 that contains the sample to be separated, a buffer reservoir bag 2, a waste bag 3, and a bag 4 wherein magnetic separation takes place. Valves 5 and 6 are positioned at the inlet and outlet of the separation bag 4, respectively, and can be operated to control the flow of fluids into and out of the separation bag 4. Another valve 7 is employed to permit pneumatic pressurization of the waste bag 3 and the separation bag 4. Such an arrangement was marketed by Baxter Health Care for their Isolex system.

Figure 2:
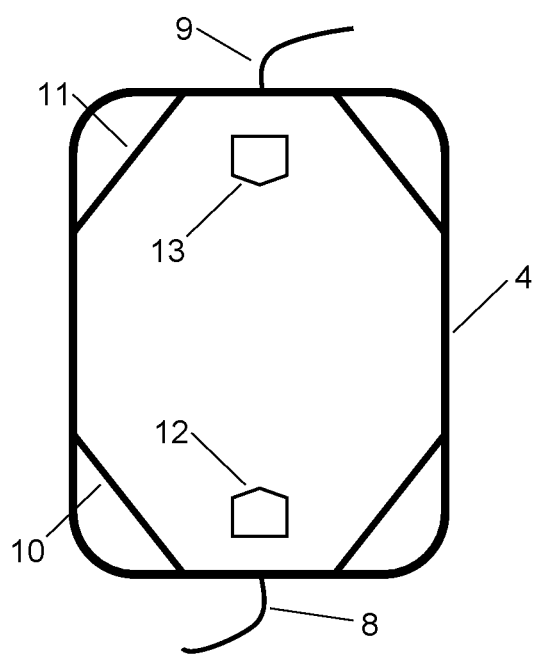
FIG. 2 depicts the bag 4 where magnetic separation takes place. In the embodiment shown, the bag has inlet and outlet ports 8, 9 on its ends for filling and/or emptying, respectively. The ends of the bag are partially tapered 10, 11 and in the partially tapered regions are flow directors 12, 13 that, in combination with the partially tapered regions, promote laminar flow.

FIG. 2 shows the separation bag 4 with inlet and outlet ports 8, 9 and partially tapered ends 10, 11 to facilitate filling and emptying the separation bag 4, respectively. In concert with the partially tapered ends 10, 11, flow directors 12, 13 promote laminar flow.

Figure 3:
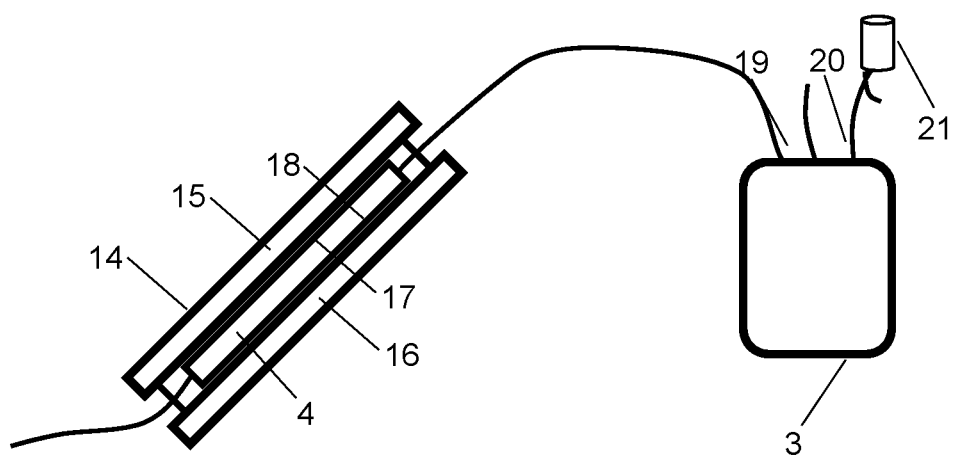
FIG. 3 shows the waste bag 3 connected to the separation bag 4 with the latter placed within a rigid frame 14 that can be rotated where one or both sides 15, 16 of the frame 14 could be, or serve as a support for, an array of magnets that could exert magnetic forces on one or both sides 17, 18 of the separation bag 4, respectively. Attached to the waste bag 3 is a port 19 that can be used to pneumatically pressurize the waste bag 3 and the separation bag 4 and a port 20 that is connected to a pressure relief valve 21.

FIG. 3 depicts an arrangement wherein the separation bag 4 is confined within a rigid frame 14 that can be rotated. In a preferred embodiment, the sides 15, 16 of the frame 14 are arrays of magnets that exert magnetic forces on one or both sides 17, 18 of the separation bag 4, respectively. In another embodiment, the sides 15, 16 of the frame 14 are passive containment walls that do not exert magnetic forces on one or both sides 17, 18 of the separation bag 4, respectively. In a more preferred embodiment, the sides 15, 16 of the frame 14 are passive containment walls which can be engaged and disengaged with arrays of magnets that exert magnetic forces on one or both sides 17, 18 of the separation bag 4, respectively. It should be noted that the frame 14 and the separation bag 4 are not horizontal so that fluids pumped into the separation bag 4 will form a meniscus that will traverse the sides 17, 18 of the separation bag 4 upon filling. Prior to filling the separation bag 4, sterile-filtered air is used to pressurize both the waste bag 3 and the separation bag 4 through a port 19. The pressure applied should be sufficient to cause the separation bag 4 to inflate so that the sides 17, 18 of the separation bag 4 engage with the sides 15, 16 of frame 14, but not excessive so as to rupture the separation bag 4 or hinder the introduction of fluids. Pressures of about 1.5 psi have been found to be appropriate to meet these requirements. A port 20 on the waste bag 3 is connected to a pressure relief valve 21 to maintain the pressure within the separation bag 4 and the waste bag 3.

The pressure relief valve 21 plays an important role in this invention. For example, in one embodiment, the separation bag 4 contains 270-315 mL and is paired with the waste bag 3 having a capacity of 2 L, where the latter is of sufficient size to accept waste from the initial magnetic separation as well as subsequent washes. The total volume of waste could be as much as 1.5 L, resulting in a four-fold pressure increase in the waste bag, potentially threatening the integrity of the system or hindering the pumping of fluids. Furthermore, without pressure relief, the increasing pressure could affect the viability of target cells. By incorporating a pressure relief valve 21 set to maintain constant pressure within the system as fluid is introduced, these problems are eliminated.

There are many advantages of using the pressurized system described above for maintaining the separation bag 4 in the rigid form as compared with a non-pressurized system. While this invention can be practiced with the separation bag 4 placed in a horizontal position, it is advantageous to rotate the frame 14 on an angle minimally sufficient to create a meniscus as the separation bag 4 is filled. When sample to be separated is pumped into the pressurized system, a clear and well-defined meniscus is visible and rises within the separation bag 4 upon filling. The visibility of the meniscus can be very helpful in the case where it is desirable to position sample to be separated within some specific region of the separation bag 4. For example, if it is advantageous to have a plug of sample positioned above the bottom of 4, a denser cell-compatible buffer (e.g., containing sucrose or some other substance that increases density) can be introduced after the appropriate quantity of sample is pumped into the separation bag 4. By that method and the ability to visualize a meniscus, sample for separation can be accurately positioned. We have found that an isotonic buffered saline solution containing 5% sucrose is adequate for positioning leukapheresis products containing as much as 10% hematocrit into the region where the sample is exposed to the magnetic gradient.

By incorporating constant pressurization, differential densities, and a rotatable frame 14, it is possible to create a process that results in recovery of highly pure target cells by 1) pumping a sample containing magnetically labeled target cells from an inlet end of a rigidly contained and pressurized separation bag 4 that is positioned on an angle sufficient to create a defined meniscus as sample is introduced and position that sample precisely within the magnetic gradient by following it with a denser buffer; 2) allowing separation to occur; 3) pumping the solution containing cells which did not magnetically separate through the outlet end of the separation bag 4 with the denser buffer; 4) introducing an air bubble into the separation bag 4 containing the denser buffer; 5) tilting the frame 14 back and forth to cause the meniscus created by the bubble therein to "scrub" the collection surface(s) to remove non-target bystander cells; and 6) repeating Steps 3-5 as required to yield the desired product. It is advantageous to alternate buffer densities in sequential steps to prevent mixing of solutions, which results in more efficient removal of non-target bystander cells. For example, after the first wash with the denser buffer is completed, the frame 14 can be tilted downwards so that the outlet end is lower than the inlet end, and less dense buffer can be pumped into the separation bag 4.

Figure 4:
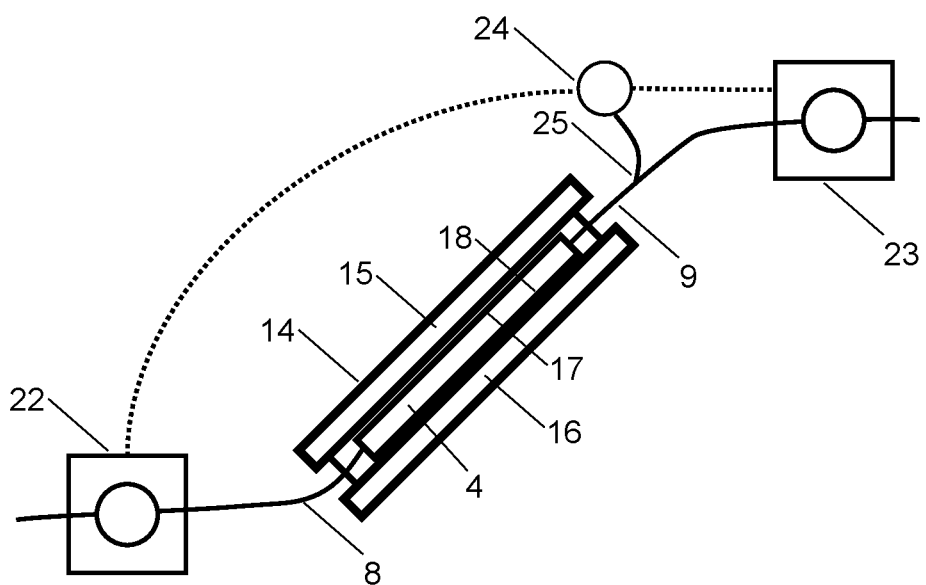
FIG. 4 shows the separation bag 4 placed within the frame 14 where one or both sides 15, 16 of the frame 14 could be, or serve as a support for, an array of magnets that could exert magnetic forces on one or both sides 17, 18 of the separation bag 4, respectively. Inlet and outlet ports 8, 9 are connected to an inlet pump 22 and an outlet pump 23 that can independently or synchronously pump fluids (solutions or gases) into or out of the separation bag 4, respectively. A pressure gauge 24 is attached to the separation bag 4 via a port 25 and provides feedback control to pump 23.
Figure 5:
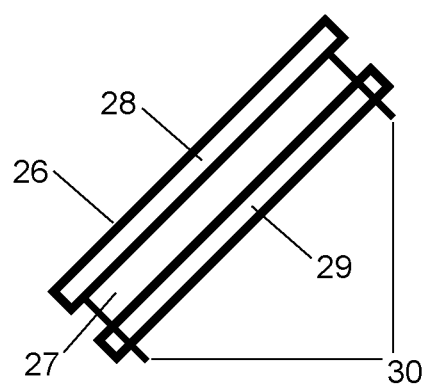
FIG. 5 shows an adjustable rigid frame 26 where the spacing 27 between the sides 28, 29 of the frame 26 can be varied using a mechanism 30 that allows one side 29 of the frame 26 to be moved in relation to the other side 28 of the frame 26.

A second solution for creating a rigid container from a flexible disposable bag that would have similar benefits as the foregoing is depicted in FIG. 4. As in FIG. 3, the separation bag 4 is held within the frame 14, and the sides 15, 16 of the frame 14 engage with the sides 17, 18 of the separation bag 4, respectively. However, in this arrangement, the separation bag 4 is attached to an inlet pump 22 through the inlet port 8 and an outlet pump 23 through the outlet port 9, where both pumps can also serve as valves (e.g., in the case of peristaltic pumps). Also depicted in FIG. 4 is a pressure gauge 24 that is attached to the separation bag 4 via a port 25. In this embodiment, the separation bag 4 essentially devoid of any air is positioned within frame 14. With the outlet pump 23 deactivated (i.e., valve closed), sample to be separated is pumped into the separation bag 4 by the inlet pump 22, thus filling the separation bag 4 and rendering it sufficiently rigid. As before, a sufficiently denser buffer (e.g., 5% sucrose) can be used to position the sample for optimal separation. Following separation, the inlet pump 22 is activated to pump wash buffer into the separation bag 4 while synchronously pumping solution out of the separation bag 4 with the outlet pump 23. In this way, the separation bag 4 maintains its rigid shape throughout the entirety of the process. The pressure gauge 24 monitors the pressure inside the separation bag 4 during the process and provides feedback to both pumps 22, 23 to prevent over- or under-pressurization. With this embodiment, the benefits of the preceding positive-pressure embodiment are realized.

An alternative approach that can also be used for magnetic separation of targeted entities to achieve similar ends as the foregoing is to employ an adjustable rigid frame 26 where the spacing 27 between the sides 28, 29 of the frame 26 can be varied using a mechanism 30. In one embodiment, the mechanism 30 would allow one side 29 of the frame 26 to be moved in relation to the other side 28 of the frame 26, thereby varying the spacing 27 between the sides 28, 29 of the frame 26. In another embodiment, both sides 28, 29 of the frame 26 would be movable by the mechanism 30, thereby permitting variation of the spacing 27 between the sides 28, 29 of the frame 26.

Such an adjustable rigid frame 26 can be deployed in the preceding positive-pressure embodiment or in the preceding two-pump embodiment. In some embodiments, the spacing 27 between the sides 28, 29 of the frame 26 can be set prior to separation to define the chamber volume and maintained throughout the entirety of the process. In other embodiments, the spacing 27 between the sides 28, 29 of the frame 26 can be set prior to separation to define the chamber volume and subsequently changed during the process to increase or decrease the chamber volume, for example during the washing steps or product recovery. In still other embodiments, the spacing 27 between the sides 28, 29 of the frame 26 can be decreased to force solution out of the separation bag 4 and into the waste bag 3, and increased thereafter to permit refilling of the separation bag 4.

To test the concept of varying the spacing 27 between the sides 28, 29 of the frame 26 while maintaining the integrity of the collection surface(s), an arrangement similar to that depicted in FIG. 3 was fabricated where the spacing 27 between the sides 28, 29 of the frame 26 could be varied from 4-14 mm. The dimensions of the sides 28, 29 of the frame 26 were 19.5×26.5 cm. One of the sides was constructed from $3/8$"-thick rigid Plexiglas to allow for visualization, while the other side comprised an array of magnets capable of inducing a magnetic field gradient. A flexible bag, approximately 12.5×25.5 cm, was obtained from a LOVO Cell Washing Disposable Kit (Fresenius Kabi, Lake Zurich, Ill.). The bag in that kit is referred to as the "in-process bag" and has ports on both ends of the longer dimension. This bag was utilized as the separation bag 4 and was positioned as in FIG. 3 with the top port of the bag connected to a second flexible bag serving as the waste bag 3. The bag used as the waste bag 3 was also obtained from the LOVO Cell Washing Disposable Kit and is referred to as the "filtrate bag" by the supplier. That bag was also connected to a pressure relief valve 21, as in FIG. 3. A peristaltic pump was connected to the inlet port 8 of the separation bag 4 identical in concept to the inlet pump 22 shown in FIG. 4. This created a system whereby, with the inlet pump 22 acting as a shutoff valve, both bags could be pressurized to 1.5 psi with a suitable fluid (e.g., air) such that the sides 17, 18 of the separation bag 4 engage with and are held tightly against the sides 28, 29 of the frame 26. As the waste bag 3 is not confined, it acts like an air bladder and inflates. For this arrangement, as liquid is introduced into the system via the peristaltic pump, it displaces an equivalent volume of air, which is released via the pressure relief valve 21 to maintain constant pressure, and thus, the system integrity.

Evaluations of the system were made at a spacing 27 of 4-12 mm. At a spacing 27 of 5 mm, the volume of the chamber was 180 mL, and at a spacing 27 of 10 mm, the volume approximately doubled, as expected. In all cases, the sides 17, 18 of the separation bag 4 engaged with and were held tightly against the sides 28, 29 of the frame 26. The functionality of this system in terms of separation performance was further tested with experiments performed using peripheral blood mononuclear cells. CD3+ cells (i.e., T cells) were magnetically labeled, and the mixture of cells (i.e., labeled target cells and unlabeled non-target cells) was pumped into chambers wherein the spacing 27 between the sides 28, 29 of the frame 26 was 5 or 10 mm. Following magnetic separation, the magnetically labeled target cells were subjected to several cycles of washes with buffer and meniscus scrubbing (i.e., rocking the entire chamber through 90°, allowing a meniscus to passage over collected cells) to remove non-target cells. At a spacing 27 of both 5 and 10 mm, the system performed satisfactorily as regards yield and purity of target cells.

The experiments described above demonstrate the utility of this invention wherein a flexible bag that can be converted into a rigid chamber of variable volume. The present system will be useful to accommodate variations in the number and concentration of total cells, the number and concentration of target cells, and the volume of sample to be processed. For example, processing $10^8$ TNC might be sufficient for many applications; however, $10^9$ TNC is typical for a leukapheresis product, while $10^{10}$ TNC is often required for stem-cell isolations. In cases where the volume to be processed becomes large enough that the magnetic field gradient applied to one side of the chamber is insufficient, it is a simple matter to employ an arrangement wherein magnetic field gradients are applied to both sides.

A variable-volume separation chamber obtained from a flexible bag in accordance with this invention is useful in other respects. The manipulations required to remove non-target cells (see co-pending application PCT/US2016/031528) involve the passage of wash buffers over the collected cells as well as the passage of menisci created by controlled introduction of air. For a separation requiring a large spacing (e.g., 10-12 mm), the meniscus that is formed might not be sufficient to rid the collected cells of entrapped non-target cells. Accordingly, it would be advantageous to employ an adjustable frame wherein the spacing can be decreased, thus reducing the chamber volume. This could be advantageous in at least three ways. Firstly, there would be a reduction in the quantity of buffer that would be required to fill the chamber for the wash cycles. Secondly, the time required for emptying the chamber would also be reduced. Finally, a bubble passaging through two plates has a greater meniscus scrubbing effect as the spacing between those plates decreases. There is likely an optimal spacing between the plates to achieve the desired goals.

Another significant advantage to employing a variable-volume separation chamber constructed from a flexible bag is that by decreasing the volume of the chamber, there will be a point where an air gap will be capable of preventing two solutions from contacting each other and mixing. To illustrate this point, consider that a blood product to be separated is introduced into a separation chamber where the spacing is 10 mm, accommodating a sample volume of approximately 360 mL. After the separation has taken place, the volume of the separation chamber can be reduced, with appropriate valving, to force solution to go to waste. By selecting an appropriate spacing, it is possible to subsequently introduce an air gap such that fresh buffer can be introduced into the separation chamber to force the remaining solution to go to waste with little or no mixing of the fresh buffer and the remaining solution.

The following examples explain the invention in greater detail.

Example 1

The following steps have been used for separating magnetically labeled CD3+ cells from leukapheresis products employing air pressure, differential densities, and gravitational effects.

1. Begin by pressurizing the waste bag to about 1.5 psi to make it rigid and connect the waste bag to the separation bag that is placed within the rigid frame (the walls of the rigid frame being on one side a planar magnetic array and the other a containment wall).

2. With the separator tilted up (outlet at the top) and the inlet and outlet valves open, pump sample to be separated into the bag at high speed (e.g., 150 mL/min).
3. Once the sample has completely entered the separation bag, switch to 5% sucrose containing 75 mM NaCl ("sucrose solution") until sucrose begins to enter the bag which positions the sample fully within the magnetic field.
4. Separate for 10 min.
5. Pump sucrose solution into the bag to push the negative fraction or supernatant up and out of the bag.
6. Once the negative fraction has been removed, tilt the separator down and begin to pump in air to form a bubble; after the appropriate amount of air (about 10% of the bag volume) has been pumped in, switch back to sucrose solution and pump just until it begins to enter the bag.
7. With both the inlet and outlet valves closed, rock the separator back and forth until the non-target cells have been re-distributed back into suspension.
8. With the separator in the upward-facing position (bubble near the outlet) and both valves open, pump in sucrose solution to remove the bubble.
9. Wait 5-10 min for any dislodged target cells to be re-captured,
10. Tilt the separator down and begin to pump non-sucrose-containing wash solution into the bag; once the sucrose wash solution has been removed, begin to pump in air to form a bubble.
11. With both the inlet and outlet valves closed, rock the separator back and forth until the non-target cells have been re-distributed back into suspension.
12. With both valves open, tilt the separator up (bubble near the outlet) and pump in non-sucrose-containing solution to remove the bubble,
13. Wait 5-10 min for any dislodged target cells to be re-captured.
14. Pump sucrose solution to push the non-sucrose-containing wash solution up and out of the bag.
15. If necessary, Steps 6-10 can be repeated to put the cells back into non-sucrose-containing solution for recovery; alternatively, the cell product can be directly recovered after Step 14 and removed from the magnetic field.

Example 2

The following steps could be used for separating magnetically labeled CD3+ cells from leukapheresis products employing air pressure, differential densities, gravitational effects, and a variable-volume chamber.
1. Begin by pressurizing the waste bag to about 1.5 psi to make it rigid and connect the waste bag to the separation bag that is placed within the rigid frame (the walls of the rigid frame being on one side a planar magnetic array and the other a translatable containment wall).
2. With the separator tilted up (outlet at the top) and the inlet and outlet valves open, pump sample to be separated into the bag at high speed (e.g., 150 mL/min).
3. Once the sample has completely entered the separation bag, switch to 5% sucrose containing 75 mM NaCl ("sucrose solution") until sucrose begins to enter the bag which positions the sample fully within the magnetic field.
4. Separate for 10 min.
5. With the inlet valve closed and the outlet valve open, decrease the chamber spacing by translating the containment wall, thereby forcing the negative fraction out of the separation bag and into the waste bag.
6. Close the outlet valve, open the inlet valve, and pump sucrose solution into the bag while increasing the chamber spacing.
7. Once the bag is full of sucrose solution, tilt the separator down and begin to pump in air to form a bubble; after the appropriate amount of air (about 10% of the bag volume) has been pumped in, switch back to sucrose solution and pump just until it begins to enter the bag.
8. With both the inlet and outlet valves closed, rock the separator back and forth until the non-target cells have been re-distributed back into suspension.
9. With the separator in the upward-facing position (bubble near the outlet) and both valves open, pump in sucrose solution to remove the bubble.
10. Wait 5-10 min for any dislodged target cells to be re-captured.
11. With the inlet valve closed and the outlet valve open, decrease the chamber spacing by translating the containment wall, thereby forcing the sucrose solution out of the separation bag and into the waste bag.
12. Tilt the separator down, close the outlet valve, open the inlet valve, and pump non-sucrose-containing wash solution into the bag while increasing the chamber spacing.
13. Once the bag is full of non-sucrose-containing wash solution, begin to pump in air to form a bubble; after the appropriate amount of air has been pumped in, switch back to non-sucrose-containing wash solution and pump just until it begins to enter the bag.
14. With both the inlet and outlet valves closed, rock the separator back and forth until the non-target cells have been re-distributed back into suspension.
15. With both valves open, tilt the separator up (bubble near the outlet) and pump in non-sucrose-containing wash solution to remove the bubble.
16. Wait 5-10 min for any dislodged target cells to be re-captured.
17. With the inlet valve closed and the outlet valve open, decrease the chamber spacing by translating the containment wall, thereby forcing the non-sucrose-containing wash solution out of the separation bag and into the waste bag,
18. Close the outlet valve, open the inlet valve, and pump sucrose solution into the bag while increasing the chamber spacing.
19. If necessary, Steps 7-12 can be repeated to put the cells back into non-sucrose-containing solution for recovery; alternatively, the cell product can be directly recovered after Step 18 and removed from the magnetic field.

Disclosed herein are means for creating a rigid chamber from a flexible and desirably disposable bag that can be used to perform multiple operations with the same facility as a chamber constructed from rigid material without the high cost of such a chamber and the difficulties of sterilizing such a chamber. The present invention also obviates the need to employ a device that maintains the engagement of the bag with either the surface of the magnet or the surface of a containment wall that mates with the magnet, which could be accomplished by placing appropriately designed vacuum plates on either side of the bag.

The present invention has broader applications than for cell separations, which may include separating a wide array of "biological entities", a term used herein to refer to various substances of biological origin, for example, cells, both eukaryotic (e.g., leukocytes, erythrocytes, or fungi) and prokaryotic (e.g., bacteria, protozoa, or mycoplasma), viruses, cell components, such as organelles, vesicles, endosomes, lysosomal packages, or nuclei, as well as molecules and macromolecules (e.g., proteins or nucleic acids, such as RNA or DNA).

The present invention has applications beyond creating a chamber for separation. It could be employed where a chamber needs to have a precise volume or some precise shape, which need not include parallel walls. It also could be employed to create a chamber within which is one or more barriers or channels. More specifically, if a bag were created while one or more surface projections were pressed into the sides of the bag, then by placing such a bag in a frame wherein the frame structure mirrors the bag structure, complex chambers can be created upon inflation of the bag. For example, if one wanted to construct a chamber that resembled a waffle, that could be accomplished as follows: 1) press the desired waffle structure into two deformable sheets, such as those used for blood bags or some other suitable material; 2) position two opposing pressed sheets and weld the edges to form a bag, with the appropriate numbers of ports in the appropriate locations; and 3) place that bag into a frame which the corresponding desired waffle structure and pressurize the bag to form the chamber. Alternatively, if sufficiently deformable materials are used for producing a bag, there would be no need to press in any structural elements as pressure exerted within the bag would be sufficient to cause the walls of the bag to conform to the desired frame structure.

A number of patent and non-patent publications are cited herein in order to describe the state of the art to which this invention pertains. The entire disclosure of each of these publications is incorporated by reference herein.

While certain embodiments of the present invention have been described and/or exemplified above, various other embodiments will be apparent to those skilled in the art from the foregoing disclosure. The present invention is, therefore, not limited to the particular embodiments described and/or exemplified, but is capable of considerable variation and modification without departure from the scope and spirit of the appended claims.

Furthermore, the transitional terms "comprising," "consisting essentially of," and "consisting of," when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step, or material. The term "consisting of" excludes any element, step, or material other than those specified in the claim and, in the latter instance, impurities ordinarily associated with the specified material(s). The term "consisting essentially of" limits the scope of a claim to the specified elements, steps, or material(s) and those that do not materially affect the basic and novel characteristic(s) of the claimed invention. All devices, device components, and methods described herein that embody the present invention can, in alternate embodiments, be more specifically defined by any of the transitional terms "comprising," "consisting essentially of," and "consisting of."

What is claimed is:

1. A method, comprising the steps of:
    converting a flexible container of a cell separating system into a substantially rigid container;
    wherein said flexible container has a first end and a second end and a pair of expansible panels joined along a periphery thereof such that facing interior surfaces of said panels form a collection space with an opening at each of said first and second ends, said openings including a valved inlet port at said first end and a valved outlet port at said second end that allow controlled fluid flow through said container and that allow positive pressure within the container to be maintained during fluid flow;
    wherein said cell separation system includes a rigid frame having oppositely facing wall members defining a confinement gap for receiving the container, at least one of said wall members including a magnet component effective to generate a magnetic field gradient in said collection space, an inlet pump attached to said inlet port and an outlet pump attached to said outlet port, thereby allowing application of positive pressure within said collection space, and a pressure gauge configured to monitor pressure inside said container and configured to control and maintain said application of positive pressure;
    wherein said converting step includes a.) placing said flexible container into the confinement gap of the rigid frame, and b.) expanding said flexible container by application of positive pressure such that exterior surfaces of said panels are urged into engagement with said oppositely facing wall members within said confinement gap, thereby rendering said container substantially inflexible; and
    separating magnetically labeled target cells from a mixed cell population within the container by and under the influence of the magnetic field gradient generated by the magnet component, said positive pressure applied to expand said flexible container being maintained throughout said separating step so as to maintain said container inflexible throughout said separating step.

2. The method according to claim 1, wherein said flexible container is a sterile, disposable bag adapted for aseptically processing biological entities.

3. The method according to claim 1, wherein said container is expanded by applying hydraulic pressure.

4. The method according to claim 1, wherein said oppositely facing wall members of said rigid frame are generally planar and substantially parallel to one another.

5. The method according to claim 1, wherein said container has at least one surface projection that directs fluid flow through said container along a predetermined flow path.

6. The method according to claim 1, wherein a distance within said confinement gap between said oppositely facing wall members is adjustable.

7. The method according to claim 1, further comprising the steps of:
    before said separating step, introducing into said collection space of said container said mixed cell population and at least one magnetic labeling agent effective to selectively bind to and magnetically label said target cells; and
    after said separating step, recovering said magnetically labeled target cells.

8. The method according to claim 7, wherein said magnet component is reversibly disengageable from said at least one oppositely facing wall member such that said magnetic field gradient in said collection space is reversibly attenuated.

9. The method according to claim 7, wherein each of said oppositely facing wall members of said rigid frame comprises a magnet component effective to generate said magnetic field gradient in said collection space.

10. The method according to claim 9, wherein said magnet component is reversibly disengageable from each of said oppositely facing wall members such that said magnetic field gradient in said collection space is reversibly attenuated.

11. The method according to claim 7, wherein, during said separating step, a wash fluid is passed through said container at least once before said recovering step.

12. The method according to claim 7, wherein said mixed cell population and said at least one magnetic labeling agent are simultaneously introduced into said collection space.

13. The method according to claim 7, wherein said mixed cell population and said at least one magnetic labeling agent are sequentially introduced into said collection space.

14. A cell separation system, said system comprising, in combination:
- a rigid frame having oppositely facing wall members defining a confinement gap;
- a flexible container disposed in said confinement gap, said flexible container having a first end and a second end and a pair of expansible panels joined along a periphery thereof such that facing interior surfaces of said panels form a collection space with an opening at each of said ends, and said flexible panels being expansible under the influence of positive pressure applied within said collection space to urge said panels into engagement with said oppositely facing wall members within said confinement gap and thereby render said container substantially inflexible;
- a valved inlet port at said first end and a valved outlet port at said second end that allow controlled fluid flow through said container and that allow the positive pressure within the container to be maintained during fluid flow;
- an inlet pump attached to said inlet port and an outlet pump attached to said outlet port, thereby allowing application of positive pressure within said collection space; and
- a pressure gauge configured to monitor pressure inside said container and configured to control and maintain said application of positive pressure;
- wherein at least one of said wall members includes a magnet component effective to generate a magnetic field gradient in said collection space; and
- wherein the system is arranged to magnetically separate labeled target cells from a mixed cell population within the container by and under the influence of the magnetic field gradient generated by the magnet component and to apply said positive pressure to expand said flexible container and maintain said positive pressure throughout magnetic cell separation of the labeled target cells from the mixed cell population so as to maintain said container inflexible throughout a cell separation process.

15. The system according to claim 14, wherein one of said oppositely facing wall members of said rigid frame is movable in relation to the other, whereby said confinement gap is adjustable.

16. The system according to claim 14, wherein said oppositely facing wall members of said rigid frame are movable in relation to each other, whereby said confinement gap is adjustable.

17. The system according to claim 14, wherein said magnet component is reversibly disengageable from said at least one oppositely facing wall member such that said magnetic field gradient in said collection space is reversibly attenuated.

18. The system according to claim 14, wherein each of said oppositely facing wall members of said rigid frame comprises a magnet component effective to generate a magnetic field gradient in said collection space.

19. The system according to claim 18, wherein said magnet component is reversibly disengageable from each of said oppositely facing wall members such that said magnetic field gradient in said collection space is reversibly attenuated.

* * * * *